US008545762B2

(12) United States Patent
Lin

(10) Patent No.: US 8,545,762 B2
(45) Date of Patent: Oct. 1, 2013

(54) SENSOR FOR DETECTING COMPOUNDS

(75) Inventor: Chhiu-Tsu Lin, DeKalb, IL (US)

(73) Assignee: Board of Trustees of Northern Illinois University, DeKalb, IL (US)

( * ) Notice: Subject to any disclaimer, the term of this patent is extended or adjusted under 35 U.S.C. 154(b) by 1332 days.

(21) Appl. No.: 10/540,607

(22) PCT Filed: Dec. 18, 2003

(86) PCT No.: PCT/US03/41000
§ 371 (c)(1),
(2), (4) Date: Oct. 26, 2005

(87) PCT Pub. No.: WO2004/099754
PCT Pub. Date: Nov. 18, 2004

(65) Prior Publication Data
US 2006/0154414 A1 Jul. 13, 2006

Related U.S. Application Data

(60) Provisional application No. 60/437,311, filed on Dec. 30, 2002.

(51) Int. Cl.
*G01J 1/48* (2006.01)
*G01N 33/00* (2006.01)
(52) U.S. Cl.
USPC .............................. 422/86; 436/104
(58) Field of Classification Search
USPC ............................ 422/86; 436/104
See application file for complete search history.

(56) References Cited

U.S. PATENT DOCUMENTS

| 2,054,885 | A | * | 9/1936 | Schroter | 436/120 |
| 3,689,224 | A | * | 9/1972 | Agnew et al. | 422/413 |
| 3,854,885 | A | * | 12/1974 | Fromm et al. | 422/86 |
| 4,275,031 | A | * | 6/1981 | Fischer et al. | 422/408 |
| 4,324,558 | A | * | 4/1982 | Obermayer | 436/85 |
| 4,842,746 | A | * | 6/1989 | Fowler et al. | 210/689 |
| 5,045,285 | A | * | 9/1991 | Kolesar, Jr. | 422/98 |

(Continued)

OTHER PUBLICATIONS

Chen, K. et al., "CO hydrogenation over zirconia supported iron catalysts promoted with rare earth oxides", Applied Catalysis A: General, vol. 158, pp. 215-223, (1997).

(Continued)

*Primary Examiner* — Lore Jarrett
(74) *Attorney, Agent, or Firm* — Evan Law Group LLC

(57) ABSTRACT

A chemical sensor having a sol-gel material affixable to a predetermined surface, and an indicator within the sol-gel, for detecting and signaling the presence of at least one chemical is provided. Also provided is an indicator for detecting and indicating a presence of at least one chemical. The indicator includes a sol-gel material affixable to a predetermined surface and an indicator within the sol-gel, for detecting and signaling the presence of at least one chemical. There is provided a method of detecting at least one chemical by applying the indicator from above to a predetermined surface of an object and indicating the presence of a chemical. A method of making a chemical sensor encapsulating within a sol-gel a detector capable of detecting and signaling a presence of at least one chemical. A decontaminating agent for removing contaminants from an area, the decontaminating agent being formed of a sol-gel material affixable to a predetermined surface and a decontaminator having an affinity for the contaminants within the sol-gel for decontaminating at least one chemical present in the area.

17 Claims, 5 Drawing Sheets

(56) References Cited

U.S. PATENT DOCUMENTS

| | | | | |
|---|---|---|---|---|
| 5,053,339 | A | * | 10/1991 | Patel ................................ 436/2 |
| 5,075,297 | A | * | 12/1991 | Bannard et al. ................ 514/183 |
| 5,200,334 | A | * | 4/1993 | Dunn et al. .................... 435/182 |
| 5,637,507 | A | * | 6/1997 | Wicks et al. ................... 436/166 |
| 5,650,311 | A | * | 7/1997 | Avnir et al. .................... 435/176 |
| 6,485,979 | B1 | * | 11/2002 | Kippenhan et al. ............... 436/1 |
| 6,730,212 | B1 | * | 5/2004 | Yamagishi et al. ......... 205/777.5 |
| 6,884,394 | B1 | * | 4/2005 | Hehenberger et al. ........ 422/404 |
| 7,354,770 | B2 | * | 4/2008 | Huebner et al. .............. 436/147 |
| 2003/0022389 | A1 | * | 1/2003 | Miller et al. .................. 436/174 |
| 2003/0224530 | A1 | * | 12/2003 | Anvar et al. .................. 436/176 |
| 2004/0109853 | A1 | * | 6/2004 | McDaniel .................... 424/94.6 |
| 2006/0019408 | A1 | * | 1/2006 | Waggoner et al. ............ 436/518 |

OTHER PUBLICATIONS

Dosoretz, C. et al., "Entrapment of parathion hydrolase from pseudomonas spp. In sol-gel glass", Journal of Sol-Gel Science and Technology, 7, pp. 7-11, (1996).

Ellerby, L.M. et al., "Encapsulation of proteins in transparent porous silicate glasses prepared by the sol-gel method", Science, vol. 255, No. 5048, pp. 1113-1115, (1992).

Moss, R.A. et al., "Metal cation micelle mediated hydrolysis of phosphonic acid esters", Langmuir, vol. 15, pp. 107-110, (1999).

Munnecke, D.M., "Enzymatic detoxification of waste organophosphate pesticides", Journal of Agricultural and Food Chemistry, vol. 28, No. 1, pp. 105-111 (1980).

Park, P.W. et al., "Characterization and CO oxidation activity of $Cu/Cr/Al_2O_3$ Catalysts", Industrial & Engineering Chemistry Research, vol. 37, No. 3, pp. 887-893, (1998).

Roigk, A. et al., "Unusual catalyst concentration effects in the hydrolysis of phenyl phosphate esters and of DNA: A systematic investigation of the lanthanide series", Inorganic Chemistry, vol. 37, pp. 751-756, (1998).

Rottman, C. et al., "Doped sol-gel glasses as pH sensors" Materials Letters, vol. 13, issue 6, pp. 293-298, (1992).

Wolfenden, R. et al., "Spontaneous hydrolysis of ionized phosphate monoesters and diesters and the proficiencies of phosphatases and phosphodiesterases as catalysts", Journal of the American Chemical Society, vol. 120, pp. 833-834, (1998).

Yang, Y-C., "Chemical detoxification of nerve agent VX", Accounts of Chemical Research, vol. 32, No. 2, pp. 109-115, (1999).

Yang, Y-C. et al., "Decontamination of chemical warfare agents", Chemical Reviews, vol. 92, No. 8, pp. 1729-1743, (1992).

Zaitoun, M.A. et al., "Chelating behavior between metal ions and EDTA in sol-gel matrix", Journal of Physical Chemistry B, vol. 101, No. 10, pp. 1857-1860, (1997).

Zaitoun, M.A. et al., "Observation of electron-hole carrier emission in the Eu3+-doped silica xerogel", Journal of Physical Chemistry B, vol. 102, No. 7, pp. 1122-1125, (1998).

Ember, L. "Form rapidly degrades chemical/biological warfare agents", The Chemical & Engineering News, vol. 77, No. 10, p. 10, Mar. 8, 1999.

Defrank, J.J., "Organophosphorus cholinesterase inhibitors: Detoxification by microbial enzymes", Applications of Enzyme Biotechnology, Plenum Press, pp. 165-180, (1991).

Fuhrmann, M. et al., "Permeable, subsurface sorbent barrier for $^{90}Sr$: Laboratory studies of natural and synthetic materials", Waste Management, vol. 15, No. 7, pp. 485-493, (1995).

Kramer, P.M., "Biosensors for measuring pesticide residues in the environment: Past, Present, and Future", Journal of AOAC International, vol. 79, No. 6, pp. 1245-1254, (1996).

Wong, P.W. et al., "The detection of hexavalent chromium by organically doped sol-gels", Materials Research Society Symposium Proceedings, vol. 346, pp. 329-333, (1994).

Zusman, R. et at., "Doped sol-gel glasses as chemical sensors", Journal of Non-Crystalline Solids, vol. 122, pp. 107-109, (1990).

* cited by examiner

SENSOR FOR DETECTING COMPOUNDS

CROSS-REFERENCE TO RELATED APPLICATIONS

This patent application is a National Stage Entry Under 35 U.S.C. 371, of PCT Application No. PCT/US03/41000, filed Dec. 18, 2003, which claims the benefit of priority of U.S. Provisional Patent Application Ser. No. 60/437,311, filed Dec. 30, 2002, both of which are incorporated herein by reference.

BACKGROUND OF THE INVENTION

1. Technical Field

The present invention relates to a sensor for detecting compounds. More specifically, the present invention relates to a sol-gel sensor capable of a color change via a charge-transfer mechanism upon detection of a chemical and surface contaminant.

2. Description of Related Art

A major goal of analyte detection research is to develop inexpensive, fast, reliable, and sensitive detectors. Unfortunately, the technologies developed to date have only met some of these goals, and no single device has sufficiently attained a majority of them.

Classical detection methods such as liquid chromatography (LC), gas chromatography (GC), and supercritical fluid chromatography (SFC), in combination with mass spectrometry, are widely used and provide accurate identification of analytes and quantitative data. However, these techniques are time consuming, extremely expensive, require sample pre-concentration, and are difficult or impossible to adapt to field use.

Biosensors (i.e., devices containing biological material linked to a transducing apparatus) have been developed to overcome some of the shortcomings of the classical analyte detection techniques. Many currently used biosensors are associated with transducer devices that use photometry, fluorimetry, and chemiluminescence; fiber optics and direct optical sensing (e.g., grating coupler); surface plasmon resonance; potentiometric and amperometric electrodes; field effect transistors; piezoelectric sensing; and surface acoustic wave (Kramer, J. AOAC Intern. 79: 1245 [1996]). However, there are major drawbacks to these devices, including dependence on a transducing device that prevents miniaturization and requires a power source. These disadvantages make such devices too complex, expensive, or unmanageable for routine analyte detection applications such as for field work or home use. Additionally, many of these devices are limited by the lack of stability and availability of the biological materials (e.g., proteins, antibodies, cells, and organelles).

Immunoassay methods can also be used for detecting certain types of analytes. In immunoassays, antibodies are developed to specifically bind to a target of interest (e.g., an analyte). By labeling the antibody (e.g., with dye or fluorescent or radioactive material), binding of the antibody to an analyte can be detected. However, immunoassay methods have limited use because they require production of antibodies against each analyte of interest. Antibodies cannot be generated against some types of analytes. Additionally, the generation of antibodies can be time consuming, expensive, and extremely difficult.

Most agricultural pesticides (APs), insecticides, and chemical warfare agents (CWAs) are organophosphorus esters that can irreversibly react with the enzyme acetyl cholinesterase, thereby inhibiting its control over the central nervous system. FIG. 1 illustrates the structure of four major CWAs and three commonly used APs.

The detection and decontamination of these highly toxic agents in production sites, stockpiles, and application (or contaminated) fields (agricultural fields and battlefields) are labor-, material-, and time-intensive using current methodologies. An indicator is needed to reduce the burden of determining what pieces of equipment are contaminated and decontaminating every piece of equipment and personnel from a suspected contaminated environment. Such a decontamination indicator should be easy to use, cost-effective, and compatible with all operational equipment. A colorimetric indicator is preferred.

Currently, no effective colorimetric indicators are available for the on-site sensing of APs and CWAs. The current on-site method for the detection of these highly toxic and deadly agents in aqueous samples uses a methylene chloride extraction, followed by a concentration step or solid-phase extraction/elution and derivatization. The samples are then analyzed by gas chromatography-mass spectrometry (GC-MS). The sample preparation and analysis are time consuming. One focus of current research is to develop fast on-site screening methods that require less sample preparation. Among the options being explored are ion-chromatography, micro high-performance liquid chromatography, micellar electrokinetic chromatography, and capillary electrophoresis. However, to date, no effective detector/indicator has been developed that is capable of being affixed to a surface.

The previously developed detection methods for CWAs are M8/M9 paper and chemical agent monitor (CAM). The paper type of chemical detector generally shows a light color change upon some chemical reactions between contaminants and color indicator on the paper (M8/M9 paper). Generally, a reasonable amount of reactive chemical agents are needed to wet the active area of the paper, and then to promote and observable color change. It is difficult to collect free liquid agent from a coarse adsorbing surface such as, fabric, soil, concrete, or on moving vehicles.

There remains a need for analyte detectors and decontaminators that provide the specificity of biosensors and the benefit of calorimetric sensors, but also provide the cost-efficiency, stability, accuracy, reliability, reproducibility, and robustness that is lacking from available technologies. In particular, development of devices that can be miniaturized with controlled shapes and that do not rely on an energy source and can be coated on a predetermined surface would also be very beneficial, particularly for routine fieldwork and home use.

SUMMARY OF THE INVENTION

According to the present invention, there is provided a chemical sensor via a charge-transfer mechanism having a sol-gel material affixable to a predetermined surface, and an indicator within the sol-gel, for detecting and signaling the presence of at least one chemical. Also provided is an indicator for detecting and indicating a presence of at least one chemical. The detector includes a sol-gel material affixable to a predetermined surface and an indicator within the sol-gel, for detecting and signaling the presence of at least one chemical. There is provided a method of detecting at least one chemical by applying the detector from above to a predetermined surface of an object and indicating the presence of the chemical. A method of making a chemical sensor by encapsulating within a sol-gel a detector capable of detecting and signaling a presence of at least one chemical. There is provided a decontaminating agent for removing contaminants from an area, the decontaminating agent being formed of a sol-gel material affixable to a predetermined surface and a decontaminator having an affinity for the contaminants within the sol-gel for decontaminating at least one chemical present in the area.

BRIEF DESCRIPTION OF THE DRAWINGS

Other advantages of the present invention are readily appreciated as the same becomes better understood by reference to the following detailed description when considered in connection with the accompanying drawings wherein:

FIG. 5A shows the initial sky blue of sensor; FIG. 5B shows the sensor 10 minutes after HD analogue added; and FIG. 5C shows the sensor 5 hours after HD analogue was added.

DETAILED DESCRIPTION OF THE INVENTION

Figure 1:
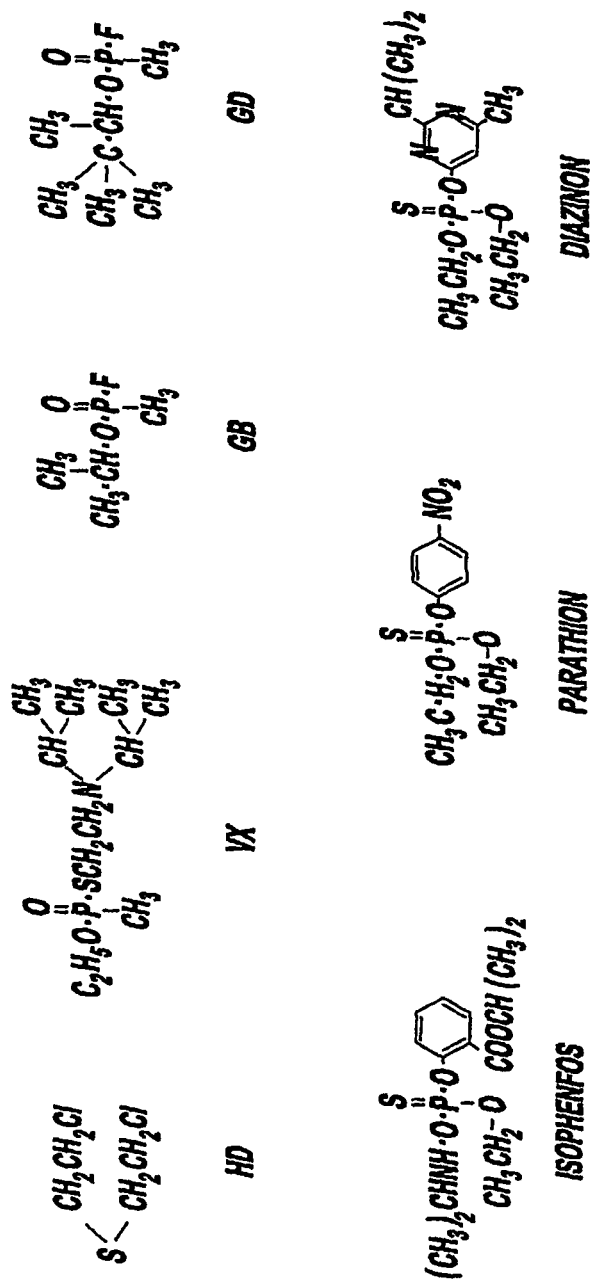
FIG. 1 shows the structure of chemical warfare agents and agricultural pesticides.
Figure 2:
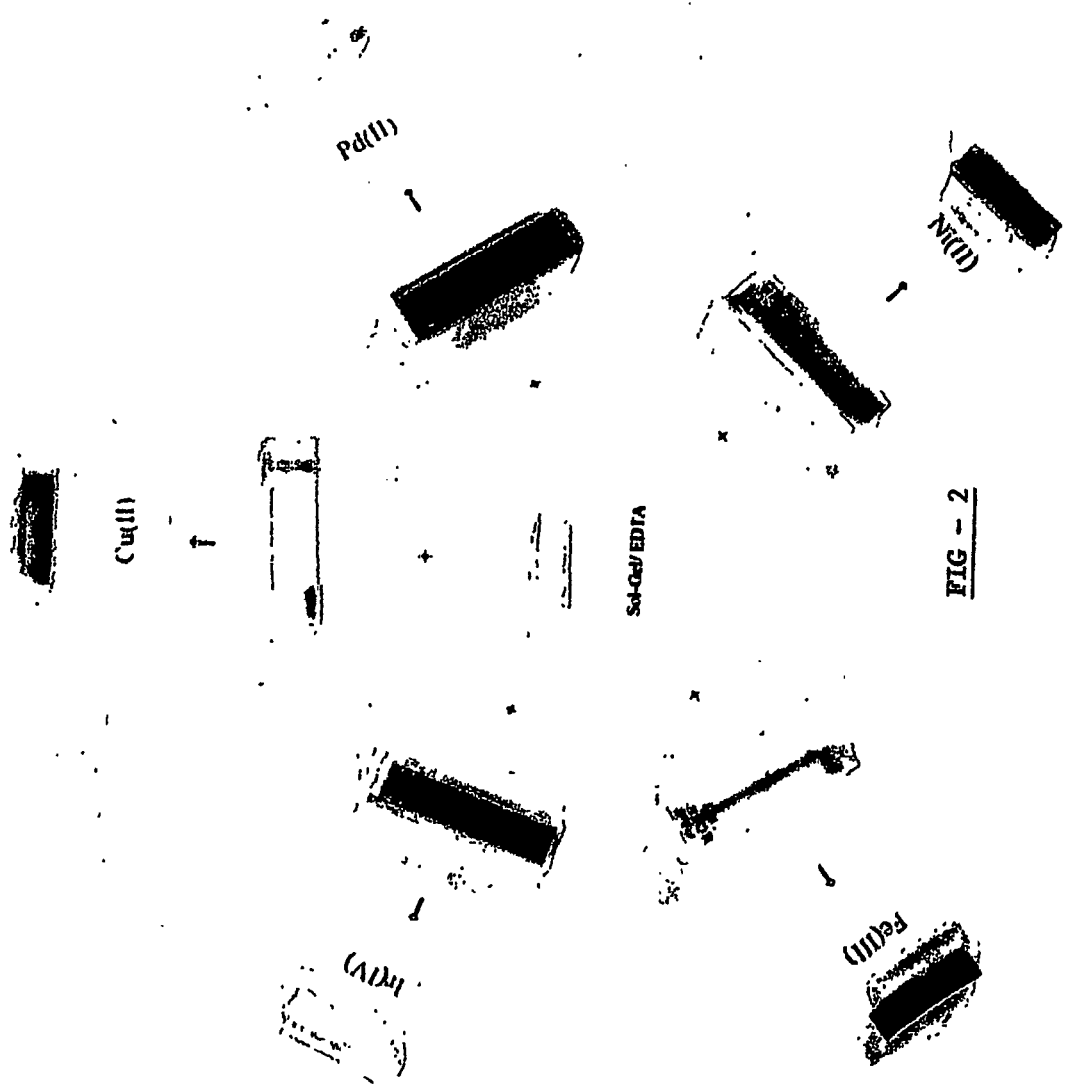
FIG. 2 shows the calorimetric detection of metal cations by EDTA-doped silica gels.

Generally, the present invention provides a sensor for detecting the presence of at least one compound. More specifically, the present invention provides a sensor or indicator that detects the presence of a compound, such as an airborne gas or other form of compound. The present invention also provides a decontaminant that cleanses the air and/or surface of the compound by capturing the compound without creating toxic byproducts.

By "sensor" as used herein it is intended to include any device that is capable of sensing the presence of at least one specific compound. The sensors of the present invention are capable of being affixed to a surface. For example, the sensors can be stuck on a person's shirt. Alternatively, the sensor can be included in a coating that is coated on a predetermined surface of an object such as a vehicle.

The sensor of the present invention can be used to detect any commonly known contaminant compounds including, but not limited to airborne contaminants, APs, CWAs, and insecticides. Other known hazardous agents can also be detected utilizing the sensor or indicator of the present invention. By way of example and not limitation, the sensor can be used to detect mustard gas (HD) and nerve gas (VX) analogues. The detection occurs via a metal-ligand charge-transfer (CT) mechanism. In this mechanism, the only time limitation is the time required for diffusion of the compound into the sensor. The sensor of the present invention can also be used to detect other compounds that are capable of being detected via a metal-ligand charge-transfer mechanism. Those of skill in the art are aware of compounds that can be identified in this manner.

The sensor produces a calorimetric change upon exposure of the sensor to a desired compound. The color change occurs immediately upon exposure of the sensor to a compound, thereby enabling the detection of a compound immediately without requiring lengthy exposure to the compound. The color change is preferably noticeable, thus eliminating the possibility of a false response. In other words, the color change is not subtle so as to prevent confusion as to whether or not exposure to the compound has occurred. The calorimetric indicators of the present invention are agent-selective and specific to a sharp color change. Highly active chromophores contained in the indicators are specially designed to produce an intense color change that is visible in standard field lighting conditions while subjected to the presence of 0.01 g/m$^2$ of a specific CWAs and organophosphorus pesticides (or insecticides). The indicator's sensitivity is high and the response time to a specific color change is short. The indicators are low-cost and easy to use in field conditions by workers or soldiers who have only limited chemical knowledge. Preferably, the colorimetric indicators for detecting APs (or insecticides) and CWAs are metal-ligand complexes, enzymes, and pH indicators, which are encapsulated in sol-gel derived silica (or zirconia) monoliths, thin filmstrips, colloidal sols and aerosols.

Figure 3:
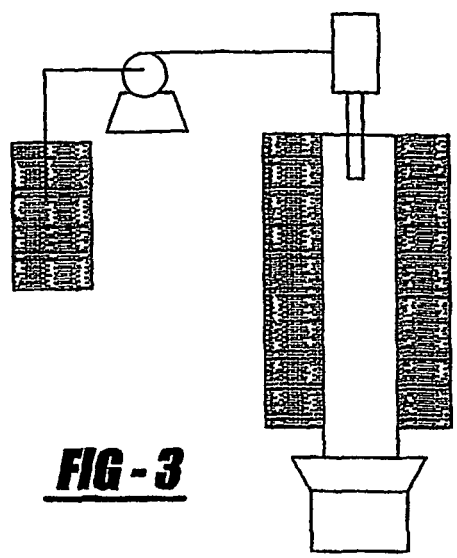
FIG. 3 is a schematic of an aerosol reactor.

By way of example, a set of seven calorimetric indicators was fabricated for detecting the agricultural pesticides (APs), such as parathion, isophenfos, and diazinon, and chemical warfare agents (CWAs), such as HD (a blistering agent), VX (a "nerve" agent), GB (Sarin) and GD (Soman) "nerve" agents. The indicators were encapsulated in sol-gel derived silica (or zirconia) matrix and processed in the forms of monoliths, thin filmstrips, colloidal sols and aerosols. Examples of the indicators include, but are riot limited to, an indicator with Cu (II), an indicator with a Lewis acid, $Cu^{2+}$/PEDTA, CuZnSOD, $Ni^{2+}$/dimethylglyoxime, thymol blue/Fichlor, thymol blue/sarinase, thymol blue/somanase, and thymol blue/parathion, hydrolase. The colorimetric indicators of APs and CWAs can also be fabricated in the forms of gel powder, colloidal sol and aerosol. Gel powder has a large active surface area, and it can act not only as a carrier, but also as an absorber. Moreover, the gel powder offers a better "blanket" coverage over the contaminated area, displays a higher sensitivity, and gives a safer detection and decontamination process. FIG. 3 illustrates a schematic diagram of an aerosol reactor for producing gel powder. The silica and zirconia sols of calorimetric indicators are pumped and sprayed via an ultrasonic atomizer. The temperature of the furnace can be adjusted to control the pore size of the silica and zirconia gel powders. The powder size can be controlled by the concentration and viscosity profiles of the sol. The colloidal sol is formed by dispersing gel powder into solvent (alcohol or water), and modified by using dispersion agent with a well-controlled pH. The fine gel powder is fluidized, which is easy to spray on the contaminated site by applying only a little pressure (similar to the air cleaner aerosol).

The present invention also provides a decontaminating device for decontaminating an area containing compounds capable of being detected by the sensor/indicator of the present invention. A catalyst is needed to accelerate the rate of chemical decontamination of organophosphorus esters and to prevent the formation of other undesired byproducts. One manner of catalyzing these hydrolytic reactions is to reduce the negative charge on the phosphate group so that nucleophiles can attack at "P═O", initiating phosphorolytic scission. Certain metal cations are efficient catalysts because they bind to P—O$^-$, mitigate the charge, and "activate" P═O. A metal cation's catalytic power generally increases with its charge: size ratio; both the water and phosphoryl activations are enhanced by higher charge density on the cation. The nanoparticle heterogeneous catalysts of $Ce^{4+}$, $Th^{4+}$, or $Zr^{4+}$ encapsulated in a high surface area of zirconia gels are preferred.

Specifically, the sensor of the present invention includes a set of nanoparticle heterogeneous catalysts, $Ce^{4+}$/zirconia, $Zr^{4+}$/zirconia, and $Th^{4+}$/zirconia, which accelerate the decontamination rate of APs and CWAs. The safety and environmental impact on the destruction process of CWA stockpiles and the contaminated AP sites, is of great concern to the general public. As substances cannot be destroyed, but can be transformed, "destruction" of CWAs and pesticides (or insecticides), consists of their irreversible catalytic conversion into compounds that can be safely disposed onto land, or into water, and air. Using the nanoparticle heterogeneous catalysts disclosed herein, the rate of hydrolysis (or phosphonate monoester cleavage) of these highly toxic agents was accelerated by a factor of about 1 to 55 million relative to hydrolysis in water at pH 7.6 and 30° C.

The sensor is preferably made utilizing sol-gel technology. More specifically, the present invention is prepared using an optically transparent xerogel. The gel contains therein an indicator that contains Cu(II), a Lewis acid, or other similar compound ($Ni^{2+}$, $Co^{2+}$, etc.) via charge-transfer chemistry, such that upon contact with the compound to be detected, the sensor visually depicts the presence of the compound to be detected.

Sol-gels are thermally stable to high temperatures and therefore, provide a suitable substrate for thermal desorption, and analysis of a wide range of organics. One embodiment of the present invention is a sol-gel material with or without surface treatment by chemical modification, such as methylation. The material of the present invention provides a useful sampling medium. The sorbent is unusually unique because of the material's high surface area, narrow pore size distribution, thermal stability and purity. The sol-gel material can be formed such that the pore size and surface area can be controlled by a hot solvent processing sol-gel method.

The sol-gel acts as a sorbent material capable of sampling, retaining, concentrating, and releasing compounds. The sol-gels can be formed using any methods known to those of skill in the art capable of producing sol-gel compositions that can be utilized without departing from the spirit of the present invention. For example, a sol-gel can be prepared by dissolving a metal alkoxide (here called the host alkoxide) such as tetraethyl orthosilicate (TEOS) in a mixture of alcohol and water, and permitting the alkoxide to undergo hydrolysis and to begin subsequent polymerization. Dopant material, which can, for example, contain a glass modifier such as erbium or calcium, or a glass former such as titanium or aluminum, is dissolved along with the metal alkoxide. If the dopant material is, for example, a salt of a glass former, the dopant species (e.g., aluminum atoms) are taken up substitutionally at metal sites in the resulting polymeric network. If the dopant material is, by contrast, a salt of a glass modifier, the dopant ions (e.g., $Er^{3+}$ ions) are incorporated at octahedral interstices in the polymeric network.

As one alternative to adding dopant material in the form of a salt, at least some dopant precursors are readily added in the form of alkoxides. The precursor alkoxides then react with the host alkoxide to form an organic polymer. This polymer is subsequently hydrolyzed and condensed to oxide glass as an associated complex. The dopant atoms or ions are atomically mixed and uniformly distributed throughout the sol and the resulting gel, and the material remains amorphous from the gel stage to the formation of the glass. Thus, the indicator/sensor of the present invention is formed by preparing a sol-gel and encapsulating the indicator of the present invention within a sol-gel.

Once formed, the sensor/indicator can be used to detect compounds that are airborne. Preferably, the sensor includes a backing that enables the sensor to be affixed to an exterior surface of a piece of clothing, a vehicle, or a person's skin.

The sensor is extremely sensitive and can detect the presence of a compound prior to any potential harm inflicted by the compound.

Further, the sensor of the present invention can be used for decontaminating objects. Decontamination, aimed at eliminating the hazard of APs (parathion, isophenfos, and diazinon) and CWAs (HD, VX, GB, and GD), is required in agriculture and on the battlefield, as well as in laboratories, pilot plants, and on chemical agent production, storage, and destruction sites. The majority of decontamination development is focused on battlefield conditions where speed and ease of application of the decontaminants are essential. Battlefield decontamination is the rapid removal of chemical agents from military vehicles, equipment, personnel, and facilities by both chemical and physical methods. The nanoparticle heterogeneous catalysts of $Ce^{4+}$, $Th^{4+}$, or $Zr^{4+}$ encapsulated in a high surface area of zirconia gels for the decontamination of APs and CWAs, are extremely effective (a 6-7 order of magnitude enhancement) and do not result in other toxic byproducts.

The invention is further described in detail by reference to the following experimental examples. These examples are provided for the purpose of illustration only, and are not intended to be limiting unless otherwise specified. Thus, the invention should in no way be construed as being limited to the following examples, but rather, should be construed to encompass any and all variations which become evident as a result of the teaching provided herein.

EXAMPLES

Example 1

The present invention provides a family of seven colorimetric indicators and three heterogeneous catalysts encapsulated in silica and zirconia gels and for use in sensing and detoxifying APs and CWAs. The first objective was the fabrication and testing of these calorimetric indicators. Effective calorimetric indicators for the decontamination of APs (or insecticides) and CWAs can be sensitive and easy to use, and can have a fast time response. Moreover, the decontamination indicator can respond specifically to a selective APs and CWAs. The specificity of a colorimetric indicator to a selective APs and CWAs can depend on the chemical nature of both agents to be detected and their associated indicators. Table 1 lists seven calorimetric indicators for detecting APs and CWAs and their color changes. Indicators (1) and (2) are based on the Lewis acid nature of $Cu^{2+}$ chelated with a ligand, propylethylenediamine triacetate (PEDTA linked to the sol-gel matrix covalently) and a protein, bovine copper-zinc superoxide dismutase (CuZnSOD), respectively. The sky blue color of $Cu^{2+}$/PEDTA and blue-green color of CuZn-SOD are resulted from the d-d transition of the $Cu^{2+}d^9$ metal ion.

TABLE 1

Colorimetric Indicators for APs and CWAs

| Indicator/Zirconia Gel | Type/Color | Agent to be detected | Expected Color Change |
|---|---|---|---|
| $Cu^{2+}$/PEDTA | A/Sky Blue | HD | Violet |
| CuZnSOD | B/Blue-Green | HD | Violet |
| $Ni^{2+}$/Dimethylglyoxime | C/Red | VX | Yellow (Green or Blue) |

TABLE 1-continued

Colorimetric Indicators for APs and CWAs

| Indicator/Zirconia Gel | Type/Color | Agent to be detected | Expected Color Change |
|---|---|---|---|
| Thymol blue/Fichlor | D/Blue | VX | Yellow to Red |
| Thymol blue/Sarinase | D/Blue | GB | Yellow to Red |
| Thymol blue/Somanase | D/Blue | GD | Yellow to Red |
| Thymol blue/Parathion hydrolase | D/Blue | Pesticides (or Insecticides) | Yellow to Red |

The sulfur mustard (HD):S(CH$_2$CH$_2$Cl)$_2$ as shown in FIG. 1, contains a non-bonding electron pair on sulfur atom that is a Lewis base. When indicators (1) and (2) are in contact with HD (a blistering agent), the reaction between Lewis base: SR$_2$, and Lewis acid Cu$^{2+}$, can alter the spectroscopic transition of the Cu$^{2+}$d$^9$ metal ion in these metal-ligand complexes. A sharp color change from sky blue to violet is expected for indicator (1) and a blue to green for indicator (2). The indicator (3) makes use of a metal-ligand charge-transfer transition in Ni$^{2+}$/dimethylglyoxime, of which the indicator color is very sensitive to chemical nature of the chelating strength and sites. When indicator (3) is in contact with the VX nerve agent as listed in FIG. 1, the chelating sites of tertiary amino group and RR'(P=O)SR" group in VX can effectively alter the Ni$^{2+}$ ligand charge-transfer band and create a color change from red to yellow (green or blue). The indicators (4)-(7) have similar characteristics. All of the indicators (4)-(7) use a pH indicator, thymol blue, to sense the hydrolytic reaction products, phosphonic, and sulfonic acids. These acids give a pH lower than 2.0 for thymol blue and display a sharp color change from blue (yellow) to red. The thymol blue is selected because it can be used in the basic range (color change from blue to yellow for a pH range from 9.6 to 8.0) as well as in the acidic range (color change from yellow to red for a pH range from 2.8 to 1.2). The decontamination processes for indicators (4)-(7) are different. For indicator (4), the VX nerve agent is oxidized by a commercial N-chloro oxidant, Fichlor (sodium N,N-dichloroisocyanurate). For indicators (5), (6), and (7), the GB nerve agent, GD nerve agent, and parathion pesticide are hydrolyzed by the corresponding enzymes, sarinase, somanase, and parathion hydrolase, separately.

The present invention also provides nanoparticle heterogeneous catalysts containing the encapsulation of Ce$^{4+}$, Th$^{4+}$, or Zr$^{4+}$ in the high surface area of zirconia gels. The general chemical processes for detoxifying APs and CWAs are hydrolysis, nucleophile-assisted substitution of HD, the oxidation of HD and VX, metal ion catalyzed hydrolysis, enzymatic decontamination and biodegradation, and catalytic oxidation. No heterogeneous catalysts containing transition metals (or rare earths) or complexes have yet been reported to catalyze the hydrolysis of APs and CWAs. Table 2 illustrates three nanoparticle heterogeneous catalysts for detoxifying APs and CWAs and their hydrolytic rate constants. The ability to rapidly hydrolyze all types of APs and CWAs, as well as ease of application and phase separation in heterogeneous catalysis, are important factors for the management of highly toxic agents. Once the agent is effectively hydrolyzed, the product effluent can be safely treated for final discharge into the environment.

TABLE 2

Heterogeneous Catalysts for the hydrolysis of APs and CWAs

| Catalysts | Reaction pH | Reaction T (° C.) | Expected k$_{obsd}$, s$^{-1}$ | k$_{relative}$ |
|---|---|---|---|---|
| H$_2$O | 7.6 | 30 | 2.0 × 10$^{-9}$ | 1.0 |
| Th$^{4+}$/Zirconia | 6.0 | 37 | 1.5 × 10$^{-2}$ | 7.5 × 10$^6$ |
| Ce$^{4+}$/Zirconia | 4.0 | 37 | 3.6 × 10$^{-2}$ | 1.8 × 10$^7$ |
| Zr$^{4+}$/Zirconia | 3.5 | 37 | 0.11 | 5.5 × 10$^7$ |

Methods and Materials

The calorimetric indicators are low cost (<$25 per indicator), have a short response time (<1 minute), and are environmentally friendly, easy to use, and portable. More importantly, the highly active chromophores contained in the indicators are specially designed to produce an intense color change that is visible in standard field lighting conditions while subjected to the presence of 0.01 g/m$^2$ of a specific CWAs and organophosphorus pesticides (or insecticides). The heterogeneous catalysts, Ce$^{4+}$/zirconia, Th$^{4+}$/zirconia, and Zr$^{4+}$/zirconia are expected to effectively and selectively speed up the rate of hydrolysis of APs and CWAs. The methods, materials, and tests are detailed below.

The Selection of Model Compounds or Stimulants.

The chemical agent stimulants were selected from the monofunctional derivatives of mustard, RSCH$_2$CH$_2$Cl (R=methyl, ethyl, or phenyl) and RSCH$_2$CH$_2$X (X-tosylate, brosylate, Br$^-$, I$^-$, or other leaving group); the VX analog, (C$_2$H$_5$O)(CH$_3$)P(O)(SC$_2$H$_5$O)(C$_6$H$_5$)P(O)(SC$_2$H$_5$); a series of organophosphorus esters similar to the G agents, dimethyl methylphosphonate (DMMP), diisopropyl methylphosphonate (DIMP), diisopropyl phosphorofluoridate (DFP), and p-nitro-phenyl diphenylphosphate (NPDP or PNPDPP); and insecticides, (C$_2$H$_5$O)$_2$P(S)(C$_6$H$_4$NO$_2$-p) (parathion), and (C$_2$H$_5$)(P(S)(OC$_2$H$_5$)(SC$_6$H$_5$) (fonofos).

Laboratory Demonstration of Colorimetric Indicators in Solutions.

Only four types of colorimetric indicators as listed in Table 1 are demonstrated in this present invention by using the "safe" chemical agent stimulants. For types A and B indicators (corresponding to indicators 1 and 2), 2-chloroethyl methyl sulfide (CH$_3$SCH$_2$CH$_2$Cl, Aldrich #24,263-2) as a Lewis base and a HD analog were used. For type C indicator (corresponding indicator 3), the neutral form of dibucaine (a tertiary amine local anesthetic drug, Sigma, #D 0513) was used to simulate the chelating sites of VX. Both VX and dibucaine have a tertiary amino group, —CH$_2$CH$_2$N(CH$_2$CH$_3$)$_2$, in addition VX has a RR'(P=O)SR" group, and dibucaine has a —(C=O)NH— group. VX is a cholinesterase inhibitor whereas, the application of dibucaine could interfere with the normal functioning of neurotransmitters (e.g., acetylcholine) that excite or inhibit neurons. For type D indicator (corresponding indicators 4, 5, 6, and 7), no "safe" reagents are available in the chemical catalog that can serve as the reaction products for the oxidation of VX by N-chloro oxidant, as well as the hydrolysis of GB nerve agent, GD nerve agent, and parathion pesticide by sarinase, somanase, and parathion hydrolase, respectively. Therefore, for the type D indicator, thymol blue (a pH indicator) was used to illustrate the color change when it is in contact with the reaction products. Since some reaction products are still very toxic or do not exist in the chemical catalog, thus only the following simulants are selected for this proposed work: ethyl methylphosphonate (CH$_3$P(O)(OH)OC$_2$H$_5$. Aldrich #38,656-1), ethanesulfonic acid (C$_2$H$_5$SO$_3$H, Aldrich #47, 155-0), fluorophosphoric acid (FP(O)(OH)$_2$, Aldrich #32, 474-4), O-ethyl methylphosphonothioate (CH$_3$P(S)(OH)OC$_2$H$_5$, Aldrich #44, 503-7).

In type A indicator, a 0.1 M PEDTA (propyl-ethylenediamine triacetate) solution is prepared using a 0.1 M phosphate buffer of pH 6.5 that is then added into an equal volume (say, 2 mL each) of a 0.1 M of Cu$^{2+}$/acetate dissolved in deionized water. The mixed solution contains Cu$^{2+}$/PEDTA complexes that display a sky blue color. In type B indicator, a $1.0\times10^{-5}$–$5.0\times10^{-3}$ M bovine copper-zinc superoxide dismutase (CuZnSOD) is prepared using 0.1 M phosphate buffer of pH 6.5 and used as colorimetric indicator. The HD analog, CH$_3$SCH$_2$CH$_2$Cl was prepared in a water/ethanol (or glycerol) solution with a concentration range of $4.0\times10^{-4}$–$1.0\times10^{-2}$ g/L. A different amount of DH analog solution (say, 0.1, 0.4, 0.6, and 1.0 mL) was added to 4.0 mL Cu$^{2+}$/PEDTA solution (type A indicator) or 4.0 mL CuZnSOD solution of a fixed molarity (type B indicator).

In type C indicator, a 0.1 M dimethylglyoxime solution is prepared using a $1\times10^{-3}$ M NaOH aqueous (or ethanolic) solution that was then added into an equal volume of a 0.1 M Ni$^{2+}$/acetate dissolved in deionized water. The mixed solution contains Ni$^{2+}$/dimethyl glyoxime complexes that display a red color. The VX analog, dibucaine, was prepared in an ethanol/water solution with a molar concentration of $1.0\times10^{-3}$ M. A different amount of VX analog solution was added to 4.0 mL Ni$^{2+}$/dimethylglyoxime complexes solution. In type D indicator, the blue color of a 0.02-0.04% thymol blue solution was prepared using a $1\times10^{-3}$ M NaOH aqueous (or ethanolic) solution. The stimulants of the reaction products of VX (ethyl methylphosphonate and ethanesulfonic acid), GB and GD (fluorophosphoric acid), and parathion pesticide (O-ethyl methylphosphonothioate) were each prepared in an ethanol/water solution with a molar concentration of $1.0\times10^{-3}$ M. A different amount of stimulant solution was added to 4.0 mL thymol blue solution. For all indicators tested, the results were recorded for a color change, the response time required for a color change, and the sensitivity and detecting limit of the selected indicators.

Laboratory Demonstration of Colorimetric Indicators in the Sol-Gel Derived Monoliths, Thin Filmstrips, Colloidal Sols and Aerosols.

Organic, metallorganic, and biological species can be encapsulated in inorganic porous glasses, via a sol-gel route at room temperature. The glass matrix serves as a solid-support for reactive materials in which the dopant molecules are capable of responding chemically to the environment through the pore space. The sol-gel doping method is gaining popularity as a result of its generality and simplicity. The sol-gel method is intermediate between impregnation and covalent bonding techniques, and it has provided a general and inexpensive route for the immobilization of reagents. The sol-gel encapsulation of chemical reactants, catalysts, and parathion hydrolase has been reported, (4, 5, 11, 13, 14) where the encapsulated chemicals are stable and their desired activities are maintained as those in solutions.

Recently, Zaitoun and Lin reported the chelating behavior between metal ions and EDTA in a sol-gel matrix. FIG. 2 shows the colorimetric detection of $Cu^{2+}$, $Ni^{2+}$, $Fe^{3+}$, $Pd^{2+}$, and $Ir^{4+}$ ions by EDTA doped silica gels. The optically transparent colorless EDTA doped sol-gel is located in the center of FIG. 2. The middle layer displays the solutions of 8.0 g/L $Cu^{2+}$, 5.0 g/L $Ni^{2+}$, 1.0 g/L $Fe^{3+}$, 0.15 g/L $Pd^{2+}$, and 0.1 g/L $Ir^{4+}$ in cuvettes. For each metal ion, 2 to 3 drops of solution were added to the EDTA doped silica gel. The resultant colored complexes of $M^{n+}$/EDTA gel remain optically transparent and are displayed in the outer layer of FIG. 2. The results in FIG. 2 indicate that all six-chelating sites in EDTA remain active in sol-gel matrix.

Following Beer's law, the spectrophotometric detection ranges of metal cations complexing with EDTA in solution are 30-8,000, 400-50,000, 4-500, 6-95, and 5-60 ppm for $Cu^{2+}$, $Ni^{2+}$, $Fe^{3+}$, $Pd^{2+}$, and $Ir^{4+}$ ion, respectively. The colored complexes of $M^{n+}$/EDTA gels shown in the outer layer of FIG. 2 were produced by adding 1.6 mg $Cu^{2+}$, 1.0 mg $Ni^{2+}$, 0.2 mg $Fe^{3+}$, 0.03 mg $Pd^{2+}$, and 0.02 mg $Ir^{4+}$ aqueous solution to the colorless EDTA doped silica gel. All $M^{n+}$/EDTA gels show a strong color and have an optical absorbance of 0.3-1.0, indicating that the detecting limit of metal ions by EDTA doped silica gels can be at least an order of magnitude better than that illustrated in FIG. 2. The response time for developing the desired color of $M^{n+}$/EDTA gels is 3, 2, 2, 600, and 900 s for $Cu^{2+}$, $Ni^{2+}$, $Fe^{3+}$, $Pd^{2+}$, and $Ir^{4+}$, ion, respectively. The high level of sensitivity in $M^{n+}$/EDTA gels is achieved because the ions are allowed to diffuse into the matrix of the gel where they react with the EDTA and remain trapped.

$SiO_2$ and $ZrO_2$ sol-gel monoliths (or strips) due to their chemical and photochemical stability, are the ideal medium for use as colorimetric indicators of APs and CWAs in field conditions by workers and soldiers. For the zirconia sol, three ml of glacial acetic acid was slowly added to 10 ml of zirconia tetrapropoxide $Zr(OC_3H7)_4$ and stirred for 30 minutes. Then 20 ml of n-propanol (or glycerol for type B indicator) was added to the solution, which was further stirred for 15 minutes at room temperature. 4 ml of 50% diluted solution of acetic acid in deionized water was slowly added to the above solution under stirring. Following this step, the solution was stirred for another 30 minutes at room temperature, filtered, and stored in a refrigerator for up to 4 days. For the silica sol, four drops of trimethoxychlorosilane are added to a stirred solution of 10 ml trimethoxyorthosilane in 20 ml n-propanol (or glycerol for type B indicator). The solution was then hydrolyzed by 3 ml of de-ionized water to obtain the silica sols. The sol-gel monoliths (or strips) of type A indicator were prepared by adding 10 mL of $Cu^{2+}$/PEDTA solution into 30 mL of either the zirconia sol or the silica sol formulated above, stirred for 15 minutes, transferred into a $0.2\times1.0\times4.0$ $cm^3$ polystyrene cuvette, and then covered with parafilm (or casted a thin film strip by using a dip-coat technique). The same procedure can be used to prepare the sol-gel monoliths (or strips) for type B, C, and D indicators, where the CuZnSOD solution, $Ni^{2+}$/dimethylglyoxime complexes solution, and thymol blue solution can be used, respectively.

The calorimetric indicators of APs and CWAs can also be fabricated in the forms of gel powder, colloidal sol, and aerosol. Gel powder has a large active surface area, and it can act not only as a carrier, but also as an absorber. Moreover, the gel powder offers a better "blanket" coverage over the contaminated area, displays a higher sensitivity, and gives a safer detection and decontamination process. FIG. 3 illustrates a schematic diagram of an aerosol reactor for producing gel powder. The silica and zirconia sols of calorimetric indicators are pumped and sprayed via an ultrasonic atomizer. The temperature of the furnace can be adjusted to control the pore size of the silica and zirconia gel powders. The powder size can be controlled by the concentration and viscosity profiles of the sol. The colloidal sol is formed by dispersing gel powder into solvent (alcohol or water), and modified by using dispersion agent with a well-controlled pH. The fine gel powder is fluidized and is easy to spray on the contaminated site by applying only a little pressure (similar to the air cleaner aerosol).

Laboratory Demonstration of Nanoparticle Heterogeneous Catalysts, $Ce^{4+}$/Zirconia, $Th^{4+}$/Zirconia, and $Zr^{4+}$/Zirconia for the Hydrolysis of APs and CWAs.

*The Chemical & Engineering News* (Mar. 8, 1999) reported that a foam for detoxifying chemical and biological warfare agents has been developed by two chemists at Sandia National Laboratories. The foam is a combination of a mild nucleophile, such as hydroxy peroxide carbonates commonly found in toothpastes, a positively charged nontoxic surfactant often found in hair conditioners, and hydrotropes found in detergents. Hydrotropes solubilize and catalyze the neutralization of the agents.

The scientific methodologies for chemical detoxification of APs and CWAs have been reviewed recently. Recently, Moss and Ragunathan reported that acidic solutions of $Zr^{4+}$, $Ce^{4+}$, or $Th^{4+}$ cations rapidly hydrolyze p-nitrophenyl methylphosphonate (PNPMP) and p-nitrophenyl phenylphosphonate (PNPPP). At pH 3.5 and 37° C., $Zr^{4+}$ enhances the rate of PNPMP cleavage by a factor of about 55 million relative to hydrolysis in water at pH 7.6 and 30° C. $Ce^{4+}$ and $Th^{4+}$ accelerate the rate of PNPMP hydrolysis by up to 18 million at pH 4 to 6. The PNPPP accelerations were all less than 1 million.

Heterogeneous catalysts are generally based on active species (notably transition metals, rare earths, metal ions or metal complexes) adsorbed on supports (such as carbon, aluminas, silicas, zeolites, clays, and ion exchange resins). The nanoparticle heterogeneous catalysts, $Ce^{4+}$/zirconia, $Zr^{4+}$/zirconia, and $Th^{4+}$/zirconia were processed via sol-gel route at room temperature. For the zirconia sol, three ml of glacial acetic acid was slowly added to 10 ml of zirconia tetrapropoxide $Zr(OC_3H_7)_4$ and stirred for 30 minutes. Then 20 ml of n-propanol was added to the solution, which was further stirred for 15 minutes at room temperature. 4 ml of 50% diluted solution of acetic acid in deionized water was slowly added to the above solution under stirring. The sol was doped during the introductory stages with metal acetates (nitrates, perchlorates, or chlorates), $M^{n+}=Ce^{4+}$, $Th^{4+}$ or $Zr^{4+}$, based on the total volume of the reagents, to produce a $1.0\times10^{-1}$ M (or higher molarity) sol at pH=3.0-5.0. Following this step, the solution was stirred for another 30 minutes at room temperature; filtered and stored in a refrigerator for up to 4 days. The gel powder of $Ce^{4+}$/zirconia, $Zr^{4+}$/zirconia, and $Th^{4+}$/zirconia were fabricated by using the aerosol reactor, as described in FIG. 3.

The construction of a nanoparticle heterogeneous catalysis reactor and the experimental details on testing the catalytic activity has been illustrated. Briefly, the catalytic activity was measured by employing an apparatus consisting of a flow reactor on-line connected to gas chromatograph (GC, Varian Star 3400Cx) having thermal conductivity detector (TCD) via six-loop-valve. The fixed-bed flow reactor was made of Pyrex tubing of 20 mm inner diameter externally heated. A fixed weight of each nanoparticle heterogeneous catalysts, $Ce^{4+}$/zirconia, $Zr^{4+}$/zirconia, and $Th^{4+}$/zirconia was placed in a sintered glass disc inside the reactor. A thermo-couple was inserted into the center of the disc for the temperature measurement. The total flow rate of the simulants, APs, and CWAs was carefully adjusted, depending on the type of reactions and catalysts used. The on-line GC-mass spectrometry, and GC-FTIR and UV-vis spectroscopy was also conducted for a detailed product analysis. Stopped-flow methodology was employed for reactions with $k>0.05 s^{-1}$.

Colorimetric Indicators for APs and CWAs are Selective, Specific, Sensitive, Easy to Use and Low Cost.

For the calorimetric detection of metal cations, the chelating agent doped silica is capable of detecting the trace amount of heavy metal ions in the contaminated water (5 ppb) with a response time of 2 to 900 seconds. A universal calorimetric indicator can be fabricated by mixing gel powders doped with two or more types of indicator compounds. The successful colorimetric indicators are expected to be low cost (<$25 per indicator), have short response time (<1 minutes), are environmentally friendly and easy to use, and portable (can be affixed on vehicles, equipment, uniforms of soldiers and workers, and facilities). More importantly, the highly active chromophores are specially designed to produce an intense color change that is visible in standard field lighting conditions while it is subjected to the presence of 0.01 g/m² of a specific CWAs and organophosphorus pesticides (or insecticides).

Zero Leaching of $M^{n+}$/PEDTA and CuZnSOD Complexes out of the Gel Matrix.

The leaching problem, occasionally encountered in sol-gel doping procedures, was solved by two methodologies: first, zirconia tetrapropoxide (or trimethoxyorthosilane) polymerization at high acidity and low water content; and second, doping with N-(trimethoxysilylpropyl) ethylene diamine triacetic acid, trisodium salt (TMSPEDTA) capable of forming a covalent bond within the encapsulating cage, resulting in the permanent anchoring of the dopant. The quality assurance, of the calorimetric indicators and heterogeneous catalysts for APs and CWAs calls for zero leaching.

Large Active Surface Area in a Nanoparticle and Enhanced Catalytic Activity of $Ce^{4+}$, $Zr^{4+}$, and $Th^{4+}$ Doped in Zirconia Gel Powders than Those in Solutions.

Gel powder has a large active surface area, and it can act not only as a carrier but also as an absorber. Moreover, the gel powder offers a better "blanket" coverage over the contaminated area, displays a higher sensitivity, and gives a safer detection and decontamination process. At pH 3.5 and 37° C., $Zr^{4+}$/zirconia enhances the rate of PNPMP cleavage by a factor of 55 million (or higher) relative to hydrolysis in water at pH 7.6 and 30° C. $Ce^{4+}$/zirconia and $Th^{4+}$/zirconia accelerate the rate of PNPMP hydrolysis by 18 million (or more) at pH 4 to 6.

The commercialization of these revolutionary calorimetric indicators and heterogeneous catalysts for chemical warfare agents and agricultural pesticides, (or insecticides) save lives not only on the battlefield and in agriculture, but also for the general public during the wartime and terrorist attacks. Fast, easy, and accurate identification of the deadly agents reduces the cost of the decontamination process and enhance the military's readiness.

Example 2

The chemical warfare agent 1,1-thiobis(2-chloroethane), commonly known as mustard gas (HD), was used extensively in World War I and stockpiled in World War II. Detection of chemical warfare agents has traditionally been accomplished by GC-MS and ion mobility mass spectrometry, and more recently by $^{31}P\{H\}$ NMR and lanthanide luminescence. These methods are reliable, but none of the instruments are portable. They also require skilled operators to interpret data, as well as detailed sample preparation to obtain analytically accurate results.

Sol-gel sensors have been reported for many different analytes, and are easy to use in field conditions by workers who have only limited chemical knowledge. Recently, cytochrome c peroxidase has been immobilized in a biogel for use as redox detectors, and EDTA-doped xerogel as a colorimetric chemical sensor for detecting heavy metal ions. The level of detection of metal cation and the response time required for forming colored metal ions/EDTA complexes, are at least an order of magnitude better than those in solution.

Recently, Brinkley, Kirkey, Marques, and Lin reported the charge-transfer complexes of Cu(II)/HD analogue in sol-gel sensors (Chemical Physics Letter, 2003, 367, pp. 39-43). A simple to use, easy to interpret, low cost, and environmentally friendly colorimetric detector of an optically transparent xerogel, based on metal-ligand charge-transfer mechanism is provided herein. HD (or its analogue) is a good Lewis base due to its lone pair electrons on the sulfur active site that can react with an indicator containing Cu(II), a Lewis acid, via charge-transfer chemistry. Formation of the charge-transfer complex was illustrated by using optical spectroscopy. The nature of complex formation with respect to the coordination and charge-transfer mechanism was interpreted by the semi empirical PM3 computational methods.

Experiments

Tetramethoxy orthosilicate (TMOS) was used as a precursor for encapsulating copper(II) acetate as dopant in sol-gel matrix. Five commercial sulfide compounds, dimethyl sulfide, chloromethyl methyl sulfide, 2-chloroethylmethyl sulfide, diethyl sulfide, 2-chlorodiethyl sulfide were selected as HD analogues. Sols were prepared using 1:4:4 mole ratios of TMOS precursor to ethanol to water, and diluted HCl were used as acid catalyst for adjusting pH values. The Cu(II) dopant concentration in the sol is $4\times10^{-3}$ M. In 1.5 ml sensor volume, several aliquots (1, 5, 10, 25, and 50 µl) of sulfide compounds were used to form color complexes, and to determine sensitivity and detection limits of the Cu(II) acetate embedded sol-gel sensors.

The colorimetric detection of HD analogue in Cu(II)-doped sol-gel sensors is observed visually and recorded spectrophotometrically. The absorption spectra were run by a HP-8452A UV-Vis diode array spectrometer. For emission studies, the sample was placed inside a liquid nitrogen optical Dewar. The 313 nm band of an Oriel 200 W Hg(Xe) lamp was isolated by using a 10 cm light path of an aqueous solution of $NiSO_4 \cdot 6H_2O$ (200 g/l) with an UG11 Schott glass filter. The emission spectra were detected by an EMI 9789QB photomultiplier tube in conjunction with a ½ m Jarrell-Ash spectrometer. Data acquisition, storage, manipulation, and digital plotting are accomplished by computer software.

The molecular structures of HD analogue, copper(II) acetate, and Cu(II)/HD analogue complexes were built by using PC Spartan Plus molecular modeling program. The equilibrium geometries were then optimized with the PM3 (parameterization method 3) methods, where the heat of formation ($H_f$), and the metal-ligand coordination and molecular orbitals involved in the formation of charge-transfer complexes were obtained.

Results and Discussion

Figure 4:
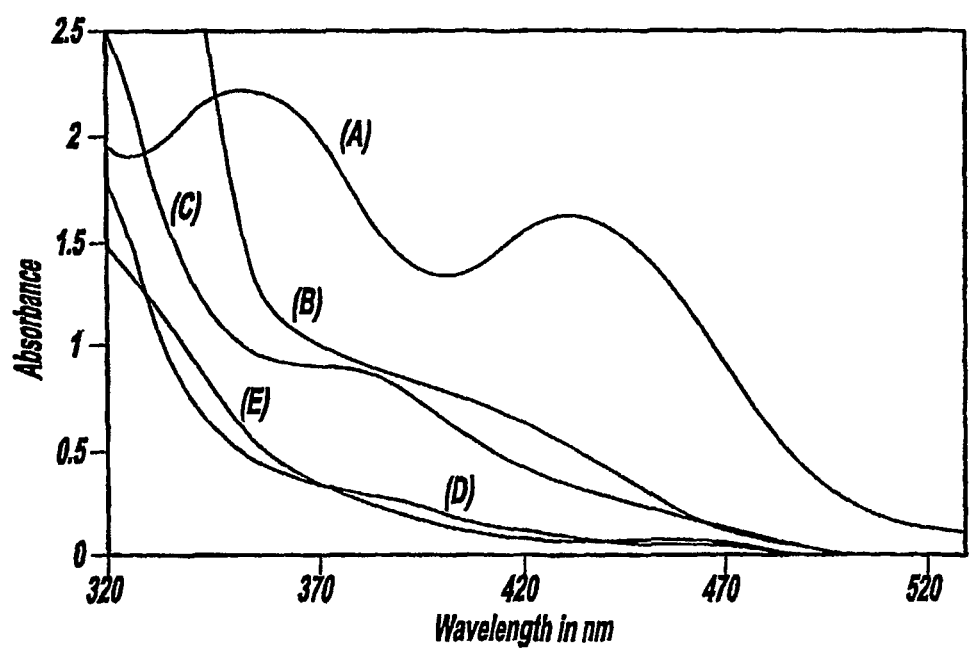
FIG. 4 is a graph depicting the absorption spectra of Cu(II)/HD analogue complexes.

FIG. 4 shows the absorption spectra of Cu(II)/HD analogue complexes: (A) 2-chloroethylmethyl sulfide in acetic acid solution, (B) chloromethylmethyl sulfide in sol-gel matrix, (C) 2-chloroethylmethyl sulfide in sol-gel matrix, (D) 2-chlorodiethyl sulfide in sol-gel matrix, and (E) diethyl sulfide in sol-gel matrix. Spectrum A shows two bands, one at 353 nm and the other at 440 nm. This corresponds to the ligand-metal charge-transfer (LMCT) bands of $R_2S$ (300-400 nm) and $RS^-$ (400-450 nm), respectively, on a Cu(II) center used for studying copper proteins. The absorption band at 440 nm was not observed for Cu(II)/HD analogue complexes in sol-gel matrix (spectra B-E), indicating that the $RS^-$ form of HD analogue exists only in acid solution but not in sol-gel matrix. The CT band for Cu(II)/HD analogue complexes in sol-gel sensors was sensitive (and specific) to the type of HD analogue. The absorption band appears at 420, 377, and 384 nm for the complexes with chloromethylmethyl sulfide (B), 2-chloroethylmethyl sulfide (C), and 2-chlorodiethyl sulfide (D), respectively. No observable CT band is shown in spectrum E. This indicates that the sol-gel sensor can give a color change only for HD analogues having at least one chlorine atom attached at different carbon backbone. It is suggested that the observed charge-transfer transition in chlorinated HD analogue may be responsible, in part, for its biological action as a blistering agent.

The charge-transfer characteristics of Cu(II)/HD analogue complexes were also observed in emission spectrum at 77 K. For example, the emission band for Cu(II) acetate-doped and 2-chloroethylmethyl sulfide-doped sol-gel, is shown at 432 and 375 nm, respectively. On the other hand, the CT emission band of Cu(II)/2-chloroethylmethyl sulfide complex in sol-gel is red-shifted to 482 nm.

Figure 5:
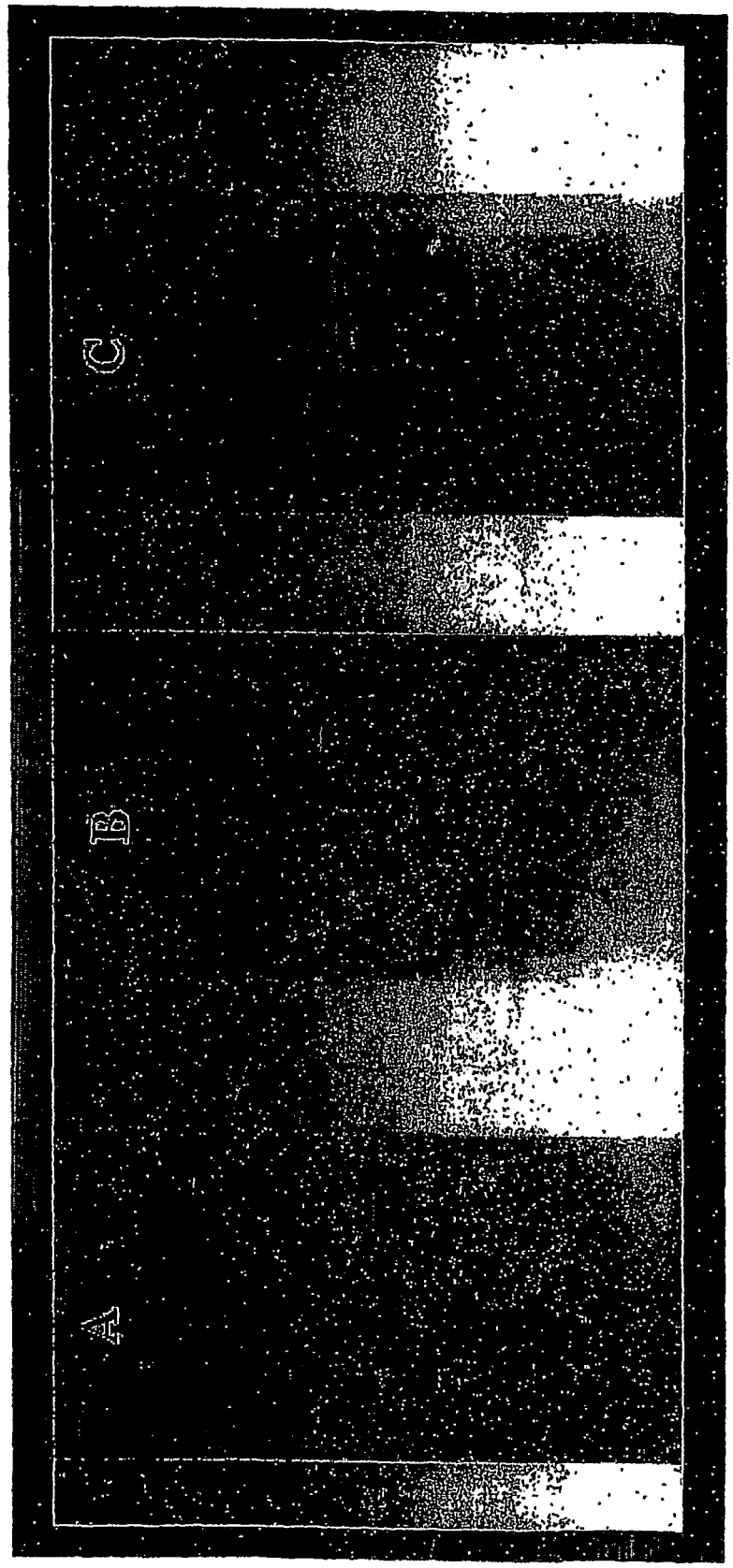
FIGS. 5A-C are photographs showing the color change of Cu(II)-doped sol-gel sensor.

The speed of visualizing a positive color change is important for the colorimetric detection of HD analogues in Cu(II)-doped sol-gel sensors. FIG. 5A shows a sky blue xerogel of Cu(II) acetate at pH 3. When a 50 µl of 2-chloroethylmethyl sulfide was added to the gel top, a color change to canary yellow is seen immediately (in seconds). For a better illustration, FIGS. 5B and C were taken approximately 10 minutes and approximately 5 hours after application of the HD analogue, respectively. The LMCT mechanism causes a color change from the sky blue color associated with the $Cu^{2+}$ ion to a canary yellow of the Cu:S charge-transfer complex, corresponding to a $Cu^+$ ion. In xerogel matrix, the response of a color change is a function of the rate of diffusion of HD analogue through the gel matrix. To achieve the rapid color change covering a large area of sol-gel sensors, a thin film (or nano-aerosol) form of Cu(II)-doped sol-gel can be used.

Figure 6:
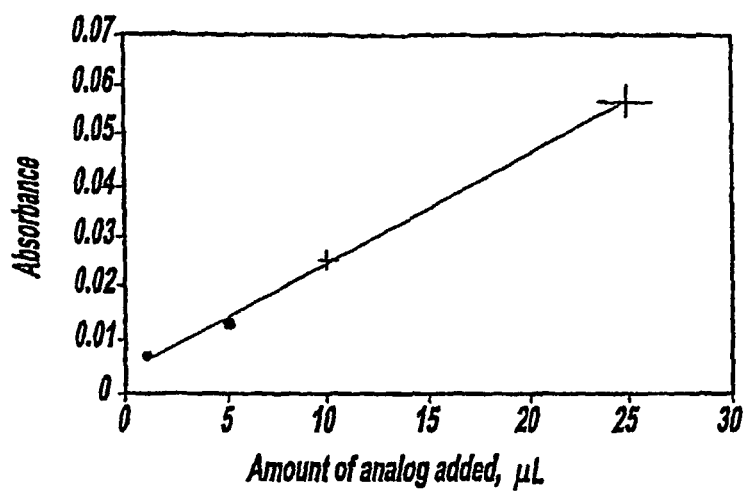
FIG. 6 is a graph showing the calibration curve of a Cu(II)-doped sol-gel sensor used for detecting 2-chloroethylmethyl sulfide.

To determine sensitivity and detection limits of the sensor, four different aliquots (1, 5, 10, and 25 µl) of 2-chloroethylmethyl sulfide were added to 1.5 ml of TMOS sol (pH 3.0) doped with $4\times10^{-3}$ M Cu(II) acetate. Six trials were performed at each sulfide level. The spectra were recorded and the corresponding absorbance at 374 nm was obtained at each concentration, using a blank sol before and after each trial to obtain a good baseline. FIG. 6 gives the calibration curve of absorbance vs. aliquot of HD analogue added to a 1.5 ml of sol-gel sol. The calibration sensitivity (i.e., the slope at the concentration of interest) for the sensor was found to be 0.002±0.001. Its detection limit (i.e., the minimum quantity of HD analogue that can be detected at a known confidence level) was determined as 0.03 µl per 1.5 ml sensor volume.

Molecular orbital calculations were carried out to investigate the effect of chlorination on the sulfide (:SRR) compounds. The molecular structures of HD analogue compounds and Cu(II)/HD analogue complexes were built by using the PC Spartan Plus molecular modeling program. The equilibrium geometries of sulfide compounds and Cu(II)/HD analogue complexes were then optimized by PM3 methods.

Table 3 displays the orbital energy and orbital compositions (i.e., a linear combination of the extent of atomic orbitals involved) of the highest occupied molecular orbital (HOMO) and the lowest unoccupied molecular orbital (LUMO) for some HD analogue compounds. Table 4 lists the calculated heat of formation ($H_f$, in kcal/mol) for some HD analogue compounds and Cu(II)/HD analogue complexes. In Table 3, the chlorination of sulfide compounds gives a greater orbital stabilization (a more negative energy) of LUMO than HOMO. The MO contributions in the unchlorinated sulfides are mainly made up of sulfur and its attached carbon atom(s). However, the chlorinated HD analogue compounds show a large extent of contribution of chlorine atom(s) in the orbital formations, especially in the orbital compositions of LUMO. A charge-transfer between sulfur and chlorine atoms is evidence that the compounds can promote the formation, and then enhance the calorimetric detection, of Cu(II)/HD analogue complexes in sol-gel sensors. The first two columns of Table 4 show an expected trend in the lowering of $H_f$ for the chlorine-substituted sulfide compounds. The last two columns of Table 4 give the following results: (1) $Cu(H_2O)_6$ is highly stable as compared to other copper complexes, such as $Cu(H_2O)_2(CH_3COO)_2$, (2) the chlorinated HD analogue gives a stable Cu(II)/HD analogue complex, e.g., $(H_2O)_5Cu:S(C_2H_4Cl)_2(H_2O)_5Cu:S(C_2H_5)(C_2H_4Cl)>(H_2O)_5Cu:S(C_2H_5)_2$, and (3) the CT complexes formed in 1:1 ratio of Cu(II):HD analogue is about 30 kcal/mol lower in energy than those formed in 1:2 ratio, and is about 150 kcal/mol lower in energy than those formed in 1:4 ratio. So, a 1:1 complex of Cu(II)/HD analogue is preferred.

TABLE 3

Energies and compositions of HOMO and LUMO for HD analogue

| HD analogue | Orbital energies (in eV) | | Orbital compositions | | | |
|---|---|---|---|---|---|---|
| | | | HOMO | | LUMO | |
| $CH_3$—S—$CH_2CH_3$ | LUMO | 0.4086 | $Sp_y$ | 0.9312 | $Sp_x$ | 0.6359 |
| | HOMO | −8.8694 | $C1p_y$ | −0.1374 | $C1p_z$ | 0.3547 |
| | | | $C2p_y$ | −0.1403 | $C2p_z$ | −0.3165 |
| | | | $C3p_y$ | −0.0130 | $C3p_z$ | 0.0754 |
| $CH_3CH_2$—S—$CH_2CH_3$ | LUMO | 0.4222 | $Sp_y$ | −0.7068 | $Sp_x$ | 0.5677 |
| | HOMO | −8.9872 | $C1p_z$ | 0.0775 | $C1p_x$ | −0.3766 |
| | | | $C2p_y$ | 0.0774 | $C2p_x$ | 0.3437 |
| | | | $C3p_x$ | 0.1145 | $C3p_x$ | −0.0419 |
| | | | $C4p_y$ | −0.1121 | $C4p_x$ | −0.0321 |
| $CH_3$—S—$CH_2Cl$ | LUMO | −0.1180 | $Sp_y$ | −0.9290 | $Sp_x$ | 0.6068 |
| | HOMO | −9.1541 | $C1p_y$ | 0.1405 | $C1p_z$ | 0.3316 |
| | | | $C2p_y$ | 0.1366 | $C2p_z$ | 0.4155 |
| | | | $C1p_y$ | −0.0499 | $C1p_z$ | 0.3054 |
| $CH_3$—S—$CH_2CH_2Cl$ | LUMO | −0.0256 | $Sp_y$ | 0.9301 | $Sp_x$ | −0.5789 |
| | HOMO | −9.1231 | $C1p_y$ | −0.1409 | $C1p_z$ | −0.2721 |
| | | | $C2p_y$ | −0.1421 | $C2p_z$ | −0.3308 |
| | | | $C3p_y$ | −0.0197 | $C3p_x$ | −0.1701 |
| | | | $C1p_y$ | −0.0499 | $C1p_z$ | −0.2515 |
| $CH_3CH_2$—S—$CH_2CH_2Cl$ | LUMO | −0.0437 | $Sp_y$ | 0.7727 | $Sp_x$ | −0.5136 |
| | HOMO | −9.2630 | $C1p_y$ | −0.0784 | $C1p_z$ | 0.3998 |
| | | | $C2p_y$ | −0.0847 | $C2p_z$ | −0.2784 |
| | | | $C3p_y$ | 0.0870 | $C3p_y$ | −0.0283 |
| | | | $C4p_y$ | 0.1307 | $C4p_z$ | 0.1591 |
| | | | $C1p_y$ | −0.0737 | $C1p_z$ | 0.1737 |
| $ClCH_2CH_2$—S—$CH_2CH_2Cl$ | LUMO | −0.1755 | $Sp_y$ | 0.7766 | $Sp_x$ | −0.5848 |
| | HOMO | −9.4299 | $C1p_y$ | −0.0893 | $C1p_z$ | 0.3632 |
| | | | $C2p_y$ | −0.0918 | $C2p_x$ | −0.3278 |
| | | | $C3p_z$ | −0.1071 | $C3p_z$ | 0.0453 |
| | | | $C4p_y$ | 0.1379 | $C4p_z$ | 0.1175 |
| | | | $C11p_y$ | −0.0915 | $C11p_z$ | 0.1385 |
| | | | $C12p_z$ | 0.0438 | $C12p_y$ | 0.0185 |

TABLE 4

The calculated $H_f$ (in-kca/mol) for sulfides and Cu(II)/HD complexes

| HD analogue compounds | $\Delta H_f$ | Cu(II)/HD analogue complexes | $\Delta H_f$ |
|---|---|---|---|
| $CH_3$—S—$CH_3$ | −10.96 | $Cu(H_2O)_6$ | −296.11 |
| $CH_3$—S—$CH_2CH_3$ | −14.06 | $Cu(H_2O)_2(CH_3COO)_2$ | −254.60 |
| $CH_3CH_2$—S—$CH_2CH_3$ | −19.99 | $(H_2O)_5Cu:S(C_2H_5)_2$ | −272.93 |
| $CH_3$—$CH_2CH_2Cl$ | −17.37 | $(H_2O)_5Cu:S(C_2H_5)(C_2H_4Cl)$ | −276.98 |
| $CH_3CH_2$—S—$CH_2CH_2Cl$ | −23.55 | $(H_2O)_5Cu:S(C_2H_4Cl)_2$ | −276.50 |
| $ClCH_2CH_2$—S—$CH_2CH_2Cl$ | −25.16 | $(H_2O)_4Cu:S_2(C_2H_5)_4$ | −246.96 |
| | | $(H_2O)_4Cu:S_2(C_2H_5)_2(C_2H_4Cl)_2$ | −249.50 |
| | | $(H_2O)_4Cu:S_2(C_2H_4Cl)_4$ | −252.51 |

CONCLUSION

An optically transparent sol-gel based sensor using Lewis acid-base chemistry for the detection of analogue of the chemical warfare agent HD, 2-chlororethylmethyl sulfide has been fabricated. The response time was fast (in seconds), and was limited by the time of diffusion of HD analogue through the sol-gel matrix. A thin film or a nano-aerosol processing technique was needed for fabricating practical sensors. The detection limit has been calibrated as 0.03 µl per 1.5 ml sensor volume. The sensor was selective to only halogenated sulfides, and more specifically, can be spectroscopically resolved based on structural features of the sulfide. The charge-transfer nature of chlorinated HD analogue is revealed from MO calculations. A 1:1 ratio of Cu(II)/HD analogue complex was preferred.

Throughout this application, various publications, including United States patents, are referenced by author and year, and patents, by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology that has been used is intended to be in the nature of words of description rather than of limitation.

Obviously, many modifications and variations of the present invention are possible in light of the above teachings. It is, therefore, to be understood that within the scope of the described invention, the invention can be practiced otherwise than as specifically described.

REFERENCES

1. Defrank, J. J. et al., In *Applications of Enzyme Biotechnoloy*, Plenum Press, 165-180 (1991).
2. Wolfenden, R. et al. *J. Am. Chem. Soc.*, 120:833 (1998).
3. Roigk, A. et al. *Inorg. Chem.*, 37:751 (1998).
4. Zaitoun, M. A. et al. *J. Phys. Chem. B.*, 101 (10):1857-1860 (1997).
5. Zaitounm M. A. et al. *J. Phys. Chem. B.*, 102:1122 (1998).
6. Fuhrmann, M. et al. *Waste Management*, 15:485-493 (1995).
7. Rottman, C. et al. *Mater, Lett.*, 13:293-298 (1992).
8. Yang, Y. C. et al. *Chem. Rev.*, 92:1729-1743 (1992).
9. Yang, Y. C. *Acc. Chem. Res.*, 32:109-115 (1999).
10. Munnecke, D. M. *J. Agric. Food Chem.*, 28:105-111 (1980).
11. Dosoretz, C. et al. *J. Sol-Gel Sci. Technol.*, 7:7-11 (1996).
12. Bishop, E. "*Indicators*" Pergamon Press: Oxford (1972).
13. Ellerby, L. M. et al. *Science*, 255:1113 (1992).
14. Zusman, R. et al. *J. Non-Cryst. Solids*, 122:107-109 (1990).
15. Welcher, F. J. *The analytical Uses of Ethylenediamine Tetraacetic Acid*, D. Van Nostrand Co.: Princeton, N.J. (1958).
16. Moss, R. A. et al. *Langmuir*, 15:107-110 (1999).
17. Clark, J. H. et al. "*Catalysis of Organic Reactions Using Supported Inorganic Reagents*," VCH: New York (1994).
18. Chen, K. et al. *Applied Catalysis A, General*, 158(1-2): 215 (1997).
19. Park, et al. *Ind. Eng. Chem. Res.* 37(3):887 (1998).
20. Wong, P. W. et al. In *Better Ceramics Through Chemistry VI*; Vol. 346, Materials Research Society, 329 (1994).

What is claimed is:

1. A sensor for detecting and indicating a presence of at least one chemical, comprising:
    a sol-gel material, and
    charge-transfer indicating means within said sol-gel for detecting and signaling a presence of at least one chemical selected from the group consisting of chemical warfare agents, agricultural pesticides, and insecticides,
    wherein said indicating means includes colorimetric signal means for signaling the presence of at least one chemical, and
    said signal means is selected from the group consisting of $Cu^{2+}$-PEDTA complex and $Ni^{2+}$-dimethylglyoxime complex.

2. The sensor according to claim 1, wherein said sol-gel is an optically transparent xerogel.

3. The sensor according to claim 1, wherein the sol-gel material comprises silica or zirconia.

4. The sensor according to claim 1, wherein the sol-gel material is a gel powder.

5. The sensor according to claim 1, wherein the sol-gel material is in the form of a monolith, a thin film strip or a colloidal sol.

6. A method of detecting a presence of at least one chemical by:
    applying the sensor of claim 1 to a predetermined exterior surface of an object; and
    indicating on the sensor the presence of at least one chemical.

7. The method according to claim 6, wherein the at least one chemical is HD or VX.

8. A sensor comprising:
    the sensor according to claim 1, and
    a backing, on said sensor, that enables affixation of the sensor to a surface.

9. A method of detecting a chemical warfare agent, comprising:
    exposing an indicator to the chemical warfare agent, which results in a color change of the indicator,
    wherein either: (1) the indicator comprises $Cu^{2+}$ and the chemical warfare agent is HD, or
    (2) the indicator comprises $Ni^{2+}$-dimethylglyoxime complex and the chemical warfare agent is VX.

10. The method according to claim 9, wherein the indicator is encapsulated in a silica or zirconia matrix.

11. The method according to claim 9, wherein the indicator comprises $Cu^{2+}$-PEDTA complex or CuZnSOD.

12. A sensor for detecting a chemical agent, comprising:
    a complex selected from $Cu^{2+}$-PEDTA complex or $Ni^{2+}$-dimethylglyoxime complex, and
    a silica or zirconia matrix, encapsulating the complex.

13. The sensor according to claim 12, wherein the matrix is in the form of a monolith, a thin film strip or a colloidal sol.

14. The sensor according to claim 12, wherein the matrix is an optically transparent xerogel.

15. The sensor according to claim 12, wherein the matrix is a gel powder.

16. A sensor comprising:
    the sensor according to claim 12, and
    a backing, on said sensor, that enables affixation of the sensor to a surface.

17. A method of detecting at least one chemical, comprising:
    applying the sensor of claim 12 to a predetermined exterior surface of an object; and
    indicating on the sensor the presence of at least one chemical.

* * * * *

UNITED STATES PATENT AND TRADEMARK OFFICE
CERTIFICATE OF CORRECTION

PATENT NO.        : 8,545,762 B2
APPLICATION NO. : 10/540607
DATED             : October 1, 2013
INVENTOR(S)       : Chhiu-Tsu Lin It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1536 days.

Signed and Sealed this
Fifteenth Day of September, 2015

Michelle K. Lee
*Director of the United States Patent and Trademark Office*